(12) United States Patent
Fu

(10) Patent No.: US 6,598,459 B1
(45) Date of Patent: Jul. 29, 2003

(54) ARTIFICIAL OLFACTORY SYSTEM

(76) Inventor: Chi Yung Fu, 1005 Duncan St., San Francisco, CA (US) 94131

( * ) Notice: Subject to any disclaimer, the term of this patent is extended or adjusted under 35 U.S.C. 154(b) by 0 days.

(21) Appl. No.: 09/223,831

(22) Filed: Jan. 2, 1999

Related U.S. Application Data

(60) Provisional application No. 60/070,284, filed on Jan. 9, 1998.

(51) Int. Cl.[7] .......................... G01N 7/00; G01N 33/497
(52) U.S. Cl. ...................................... 73/23.34; 73/24.06
(58) Field of Search ................................ 73/23.2, 23.34, 73/24.06, 31.02, 31.05, 31.06; 422/90

(56) References Cited

U.S. PATENT DOCUMENTS

| | | | | |
|---|---|---|---|---|
| 4,717,673 A | * | 1/1988 | Wrighton et al. ............ 350/357 |
| 5,063,164 A | * | 11/1991 | Goldstein .................... 436/169 |
| 5,086,286 A | * | 2/1992 | Yasukawa et al. ........... 73/23.2 |
| 5,151,110 A | * | 9/1992 | Bein et al. ...................... 55/75 |
| 5,364,797 A | * | 11/1994 | Olson et al. ................. 436/501 |
| 5,589,396 A | * | 12/1996 | Frye et al. ..................... 436/73 |
| 5,620,597 A | * | 4/1997 | Andelman ............... 210/198.2 |
| 5,880,552 A | * | 3/1999 | McGill et al. ............... 310/328 |
| 6,004,436 A | * | 12/1999 | Ayers ..................... 204/157.15 |
| 6,010,616 A | * | 1/2000 | Lewis et al. .................. 73/23.2 |
| 6,025,036 A | * | 2/2000 | McGill et al. ............... 427/492 |
| 6,051,189 A | * | 4/2000 | Wick et al. ................. 73/28.01 |

* cited by examiner

Primary Examiner—Edward Lefkowitz
Assistant Examiner—Michael Cygan

(57) ABSTRACT

The artificial olfactory system is an ultra-sensitive and selective odor sensing system for the detection of odorant molecules down to the part per trillion level. The system includes multiple ultra sensitive frequency sensors, such as sensors based on piezoelectric substrates or micro-machined resonators, capable of detecting frequency changes resulting from the interaction of odorant molecules with the sensor. A coating applied to the sensor greatly increases the surface of interaction between the odorant molecules or biological agents and the sensor. An array of these sensors, each responding to the interaction of an odorant molecule species but in a different manner, results in different frequency shifts. An ultra sensitive frequency measurement device measures as small as part per billion shift in frequency. An intelligent processor based on artificial neural networks and other intelligent signal processing system detects, recognizes, and generalizes the signature resulting from the collective response of all the sensors.

16 Claims, 8 Drawing Sheets

ARTIFICIAL OLFACTORY SYSTEM

This application claims priority of provisional application No. 60/070,284 filed Jan. 9, 1998.

BACKGROUND OF THE INVENTION

The invention relates generally to chemical sensors, and more particularly to artificial olfactory sensors.

Odors are complex mixtures of chemical species, and so contain hundreds, if not thousands, of constituent molecules. The biological olfactory system is a remarkable sensor which has some very important characteristics. There are very many olfactory cells or odorant receptors, but there are not very many different types of olfactory cells. The characterization of a scent or odor is not through a specific receptor or a specific type of receptor but through the combined response of many of the receptors. In effect, the sensors respond broadly to a range or class of odors rather than to a specific one. This is the opposite to the ideal gas sensor, which responds to only one gas, and provides a unique output for a selective species. Identification of the odor is through pattern recognition in the olfactory bulb and the subsequent neural processing in the brain. In addition, the signal-processing system removes drift and may enhance the overall sensitivity of the system by as many as three orders of magnitude. The entire system is highly compact and consumes extremely low power.

Given that the human olfactory system has 100 million olfactory cells (50 million per nostril) and that each cell has ten or more cilia, each with an odor receptor, a person has a total of 1,000 million or 1 billion odor receptors. But since there are only about 1000 types of olfactory receptors, there are thus approximately 1 million identical odor receptors of each type. This high degree of redundancy could provide for an improved ratio of signal to noise.

The ability to sense odors, or identify chemical species by their odors, has a wide range of applications. It can be deployed in many major and diverse industries such as: foods (e.g., quality control for wine and coffee), cosmetics (e.g., perfume), safety (e.g., explosive detection for airlines and bacteria detection such as the *E. coli*), humanity (e.g., detection of landmines), medicine (e.g. detection of pneumonia and some other infections), automobile (e.g., exhaust detection for pollution and fuel efficiency), etc.

In the case of explosive detection, it is particularly important and timely because, unfortunately, almost all of the most advanced and promising detection systems have some limitations in terms of what can be detected and where they can be used. Detectors which use radiation such as X-ray and other energetic particles cannot be used on human beings. These systems are intended primarily for baggage inspection. Furthermore, these technologies have not adequately addressed non-explosive devices that deliver chemical agents and they certainly are too expensive for consumer types of applications (such as quality control for coffee and wine), not to mention that they are totally inadequate for such jobs.

Practical options of detecting dangerous substances such as explosives include the use of dogs or vapor/particle detection devices. The importance of the K-9 approach stems from the high sensitivity of the dog's olfactory system and the relatively low probability of false alarms. However, there are many limitations in using canines, including short attention span, mood changes, vulnerability to illnesses such as flu, the need to be retrained in new locations, and the apparent difficulty in finding samples placed higher than five feet. Vapor/particle detectors typically depend on classical spectrometric techniques, which rely upon the identification of specific molecules, and are not as sophisticated as the olfactory senses of animals. Thus, a suitable artificial olfactory device would provide tremendous strides in the detection of explosives and the 110 million uncleared landmines around the world since such a system will not have the same limitations at those found in the use of canines. The detection requirements for counter-terrorism and mine sweeping are quite similar. In both situations, the detection systems should be sensitive, reliable, low cost, and fast.

There have been many attempts in the past to mimic the biological olfactory system. Most of them are based on existing gas-sensor technologies and have many drawbacks. Gas sensors made from $SnO_2$ are typical of current technology, and several commercial "electronic noses" have been based on $SnO_2$ arrays. Platinum pellistor-type elements, similar to $SnO_2$ sensors, require a high power consumption, which interferes with portability and low power operation.

Sensor arrays have also been made from conducting organic polymers. However, there are only a few classes of stable conducting polymers and at the present time the conducting polymers must be synthesized electrochemically, which tends to produce insoluble, intractable materials. Additional variations in the array elements have been limited to such things as varying the substituents on the polymer backbone.

The scope of conducting polymer-based sensors has recently been broadened through the use of a set of polymer blends that possess a common conducting element, polypyrrole, for signal transduction, and a variety of insulating organic polymers to achieve chemical diversity in the array. It is suspected that polypyrrole and the odor molecules incorporated into the conducting polymer act as dopants and thus produce changes in its electrical resistance. These devices function quite well, but the long-term stability of polypyrrole is of concern for practical implementation of such systems.

At the California Institute of Technology, an array of chemiresistors is used. The chemiresistors are formed of a mixture of a conducting element (e.g., carbon or polypyrrole) with a non-conducting polymer. Its detection limit currently is low but is still many orders of magnitude less sensitive than biological odor-detection systems. In addition, there are questions about the manufacturability of such sensors, since according to percolation theory, the optimal region of operation occurs at the high-gain section, which is extremely sensitive to the amount of carbon. A 1% change in the amount of carbon black can result in more than 6 orders of change in the magnitude of the resistance in that region of operation. On top of that, it also relies on a mechanism that might suffer drift or miscalibration if exposed to high concentrations, since if the swelling is great enough, the carbon grains might rearrange themselves when it shrinks back.

At Tufts University, an array of fiber-optic sensors is used as an artificial nose. The sensors contain spatially-separated photopolymers containing analyte-sensitive fluorescent indicators on an imaging fiber tip. One important advantage is that many different sensors can be built on the distal end. Though the size of each of the sensing regions is about 30 microns, thus allowing a closely-packed structure, the overall size of the sensing system is large, and more than offset the potentially small size of the fiber itself. The cited overall 60% correct prediction rate is clearly not acceptable. There is also a question on the possibility of long-term drifts of the sensitivities of these sensors, since the solvatochromic dyes are subject to continuous illumination and may react with the gases that are being sensed.

It is thus an objective to develop an artificial olfactory system to meet the above critical needs and challenges. If an artificial olfactory system can be modeled after biological systems, it has the potential to be as sensitive as its biological counterparts; as a result, one of the most important advantages is that it can be used on humans and thus could potentially detect suicide bombers. The system could also be useful for the detection of land mines, non-nitrated explosives, explosive liquids and incendiaries. The olfactory system would be capable of detecting chemicals of many kinds, provided that they have sufficient outgassing to be detected.

Specifically, it is desired to provide a low-cost, ultrasensitive, highly miniaturized (concealable), battery-powered, electronic chemical-sensing system, that is, an artificial olfactory system that would cost about a thousand dollars or less in a package about a few cubic inches (excluding the battery) with a detection limit of 100 ppt or less without pre-concentration or less than 1 ppt with pre-concentration.

SUMMARY OF THE INVENTION

The invention is an artificial olfactory system which includes materials, methods, apparatus, and intelligent processors for the detection of odorant molecules or biological agents or any other chemical or biological species in a surrounding fluid, e.g., air. The apparatus includes a sensor having first and second conductive elements (e.g., electrical contacts) electrically coupled to a chemically or biologically sensitive acoustic device (such as a quartz crystal microbalance(QCM), surface acoustic wave device (SAW), or micro-machined resonator) which provide an electrical path between the pair of conductive elements. The acoustic device is a resonator coated with aerogel or other equivalent material (such as nanotubes, porous carbons, zeolites) or with a material formed by certain methods (such as micro-machining) to expand the detecting surface area of the uncoated resonator by a large amount (by a factor of 1000 or better). The aerogel or other surface area increasing material is coated with a polymer or equivalent material that can be tuned for the attachment of the odorant molecules or biological agents or other chemical or biological species. An indirect means to detect a biological agent is to have a reactive substance, such as appropriate protein, that reacts with the biological agent resulting in the generation of odorant molecules that can then be detected by the invention. In use, the resonator provides a difference in resonating frequencies when contacted with a fluid containing odorant molecules or biological agents at different concentrations. The artificial olfactory system uses a plurality of these sensors, each with a different response to particular odorant molecules or biological agents.

The resonating frequency is typically in the megahertz range. Variability in sensitivity from sensor to sensor is conveniently provided by qualitatively or quantitatively varying the aerogel or its equivalent materials and the polymer or its equivalent materials. For example, in one embodiment, the aerogel material in each sensor is held constant (e.g., certain type of aerogel known as xerogel) while the organic polymer varies from sensor to sensor. Arrays of these sensors are constructed with at least two sensors having different chemically sensitive polymers providing dissimilar differences in resonating frequencies. The artificial olfactory system is constructed by using such an array in conjunction with a frequency measuring device electrically connected to the conductive contacts of each sensor. The artificial olfactory systems also incorporate a variety of additional components including signal processing hardware and software to determine the identity, etc. Methods of making and using the disclosed sensors, arrays, and artificial olfactory systems are also provided.

DETAILED DESCRIPTION OF THE INVENTION

The present invention attempts to mimic the functions and abilities of the biological olfactory system. While the invention is described particularly with respect to detecting odorant molecules, it more broadly encompasses detection of all chemical or biological species. Thus the term odorant molecules is generally used herein to cover any detectable species. The artificial olfactory system is based on "reproducing" the same set of characteristics as described above. As a result, it is necessary to create many identical "receptors" or sensing elements for each type of sensor. Furthermore, the sensors should respond broadly, rather than specifically as in the case of an ideal gas sensor. In addition, the system should provide advanced signal processing and intelligent information extraction as well as the ability to generalize as the biological system. And the hardware should consume very little power to allow battery operation. All these features are provided by the present invention.

There are, on the average, in the biological olfactory system, about one million identical odor receptors of each type. This redundancy is extremely important because it may be responsible for increasing the probability of "catching"

the few odorant molecules and also possibly to provide this amplification through strengthening the overall response to each odor. Thus the sensor of the invention provides many identical "receptors" or sensor elements to allow this amplification and to catch odorant molecules at low concentration. A thousand, or possibly even a million, times increase in redundancy or amplification, will provide the desired level of sensitivity of the olfactory cells. To achieve such redundancy or amplification, assuming that each sensing element occupies a certain amount of area, many redundant "olfactory receptors" are provided by increasing the detection area. Aerogel technology is used to achieve a hundred-fold to possibly even a million-fold increase in surface area by expanding the sensor surface into the third dimension; the extremely high specific surface area of aerogel simulates the many redundant olfactory receptors. Other surface increasing materials which also achieve similar increases in surface area can be used in place of aerogel.

Figure 1A:
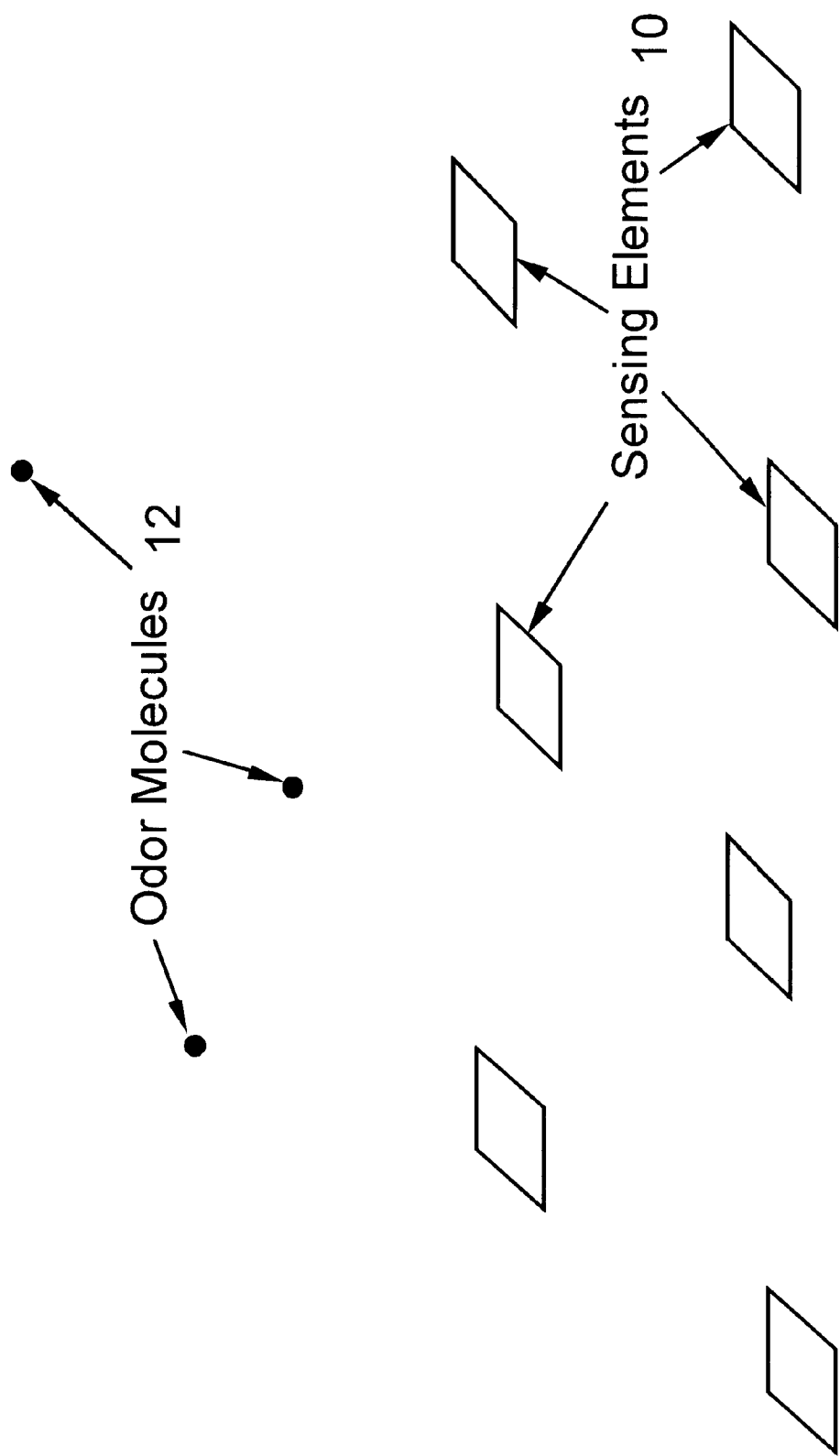
FIG. 1A shows many discrete and separated sensing elements used to simulate the effect of the great number of cilia in a biological olfactory system.
Figure 1B:
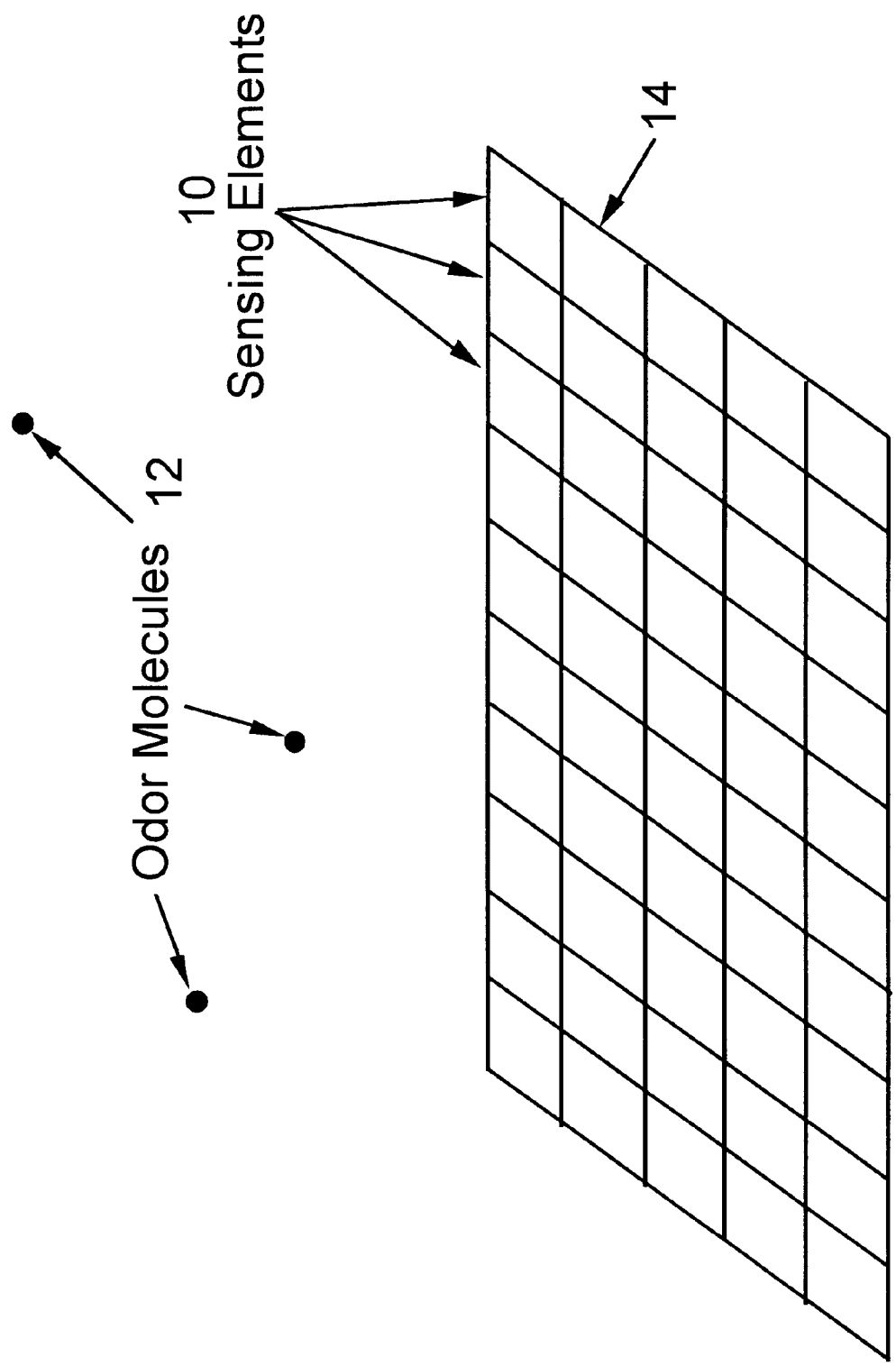
FIG. 1B shows many discrete sensing elements of FIG. 1A aligned in an integrated unit.
Figure 1C:
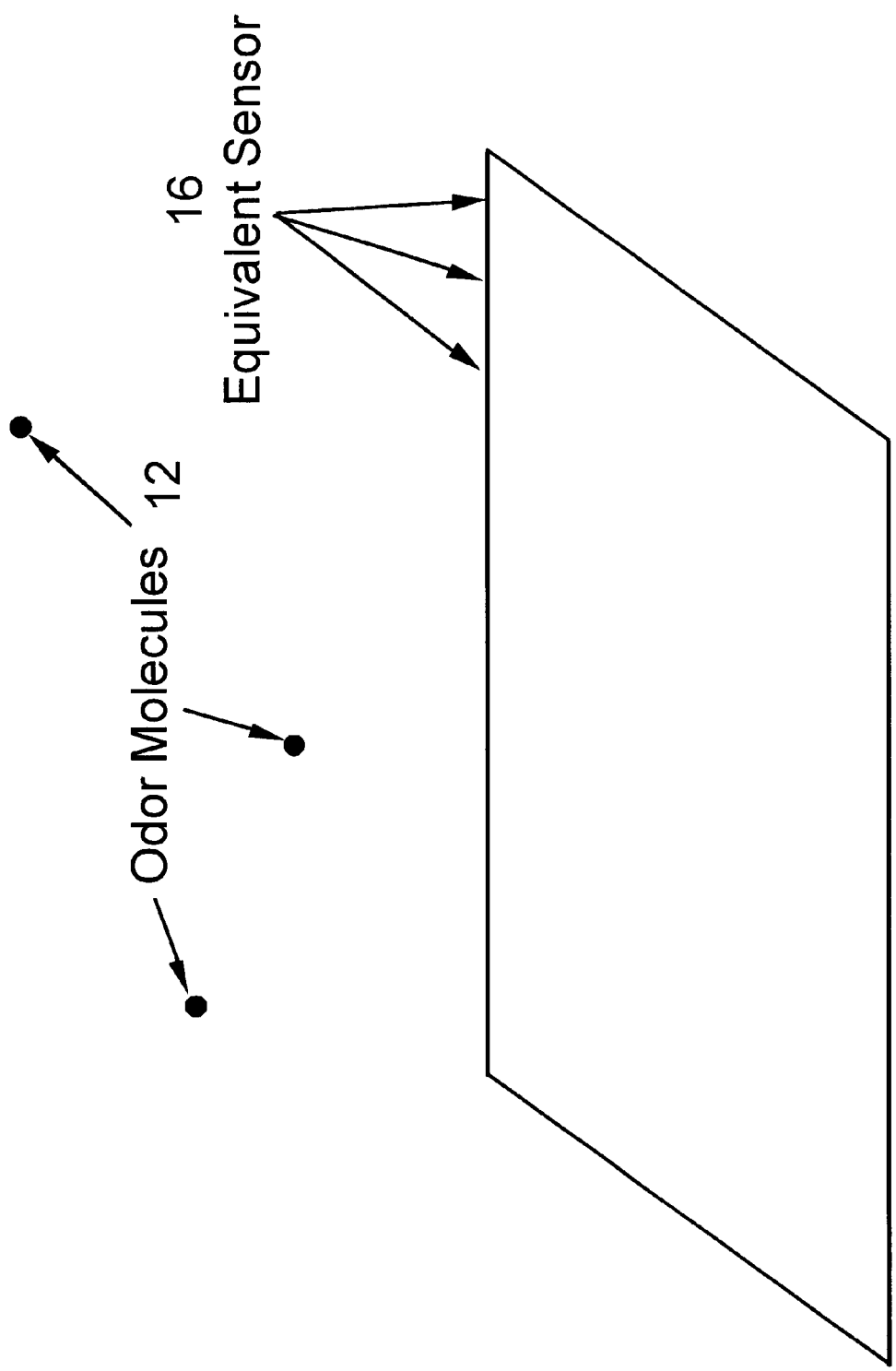
FIG. 1C shows a single sensing element with greatly expanded sensing surface area to mimic the cilia in a biological olfactory system.

FIGS. 1A–C illustrate the principles of the invention in mimicking the large number of cilia in the biological nose. As shown in FIG. 1A, a plurality of discrete and separate sensing elements 10 are arranged to detect odor molecules 12. A distributed sensor system as in FIG. 1A cannot be made very compact. In FIG. 1B, the separate sensing elements 10 have been integrated into a single structure 14. In FIG. 1C, an equivalent sensor 16 having an increased surface area according to the present invention replaces the structure 14 of FIG. 1B, providing much higher sensitivity.

The sense of smell arises from the stimulation of the olfactory system by odorant molecules emitted from an object of interest. Odorant molecules are typically hydrophobic and polar. For example, the odor of lemons comes from Limonene, which is a single molecule. However, most natural smells are complex mixtures of chemical species and so contain hundreds, if not thousands of highly complex molecules. For example, for the monitoring of the flavor of beers, the use of conventional analytical tools (e.g., gas chromatography) is not only expensive and time-consuming but also inexact due to a lack of sensitivity or quantitative information. Many different types of olfactory cells or types of sensors are needed to respond to the many different types of odors and these sensors have to be "coupled to" or "react with" the odor molecules. Because of the polar nature of many of the odorant molecules, polymers are used in the sensor elements of the invention, since the charges of parts of the molecule can act as "handles" to which polymers could be "tuned" to specifically attach. In addition, different molecules will have different solubilities in these polymers; and the amount of swelling will also be different. These three different effects enhance the chemical diversity and thus allow detection of a broad range of smells as in the case of a biological nose. There are many different variants or types of polymers to choose from, thus allowing many types of sensors needed to make an artificial olfactory system. Thus, different types of polymers are used on aerogels for forming the different types of sensors. In addition, materials other than polymers can also be used as long as odorant molecules will attach to them.

Many techniques and devices can be used to measure the amount of attached odorant molecules. One preferred way is to measure the frequency shift of a piezoelectric crystal attached to the polymer-coated aerogel when these molecules are coupled onto that polymer. A quartz-crystal microbalance (QCM) is one type of apparatus and can detect crystal frequency shifts with an extremely high degree of sensitivity. One model claims a precision of as good as +/−0.005 Hz out of 6 MHz or about 1 part in a billion. However, any method or apparatus which can detect a change produced by attachment of the odorant molecules, e.g., any effect caused by a change in mass, stress, or swelling of the polymer film of the sensor due to adsorption, absorption, or imbibition of an odorant molecule, can be used.

Pattern recognition and intelligent signal processing are used for identifying odors with a minimum of false alarms. And among the various sorts of intelligent systems such as expert systems, artificial neural networks, and fuzzy logic, artificial neural networks and fuzzy logic are more appropriate for this application than expert systems. Thus the desired information is extracted from the inputs with neural networks, i.e., the frequency shifts in the resonant frequencies of a plurality of crystals caused by contact with different chemical species of the polymer coated aerogel attached to the crystals, are inputs into a neural network or other intelligent systems for pattern recognition signal processing.

Figure 2A:
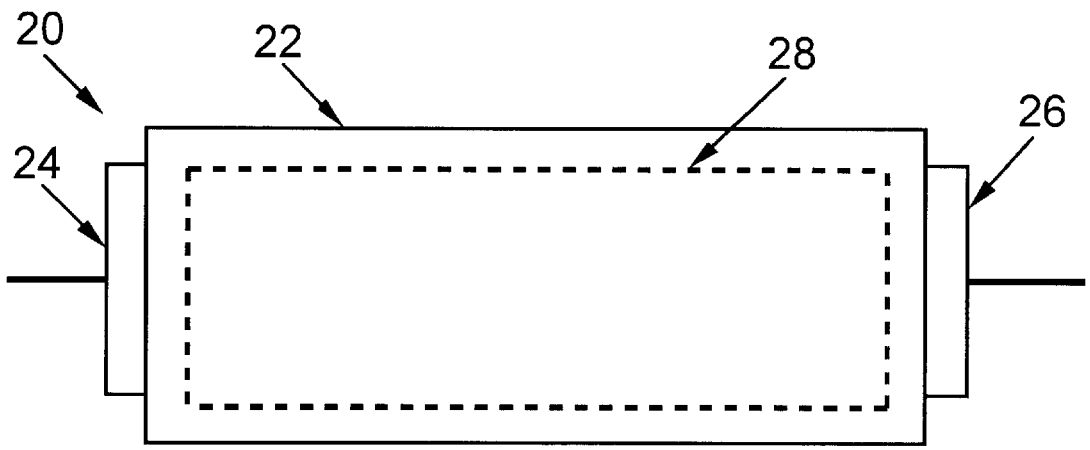
FIG. 2A is a top view of a sensor with electrical contacts on each end of a sensor substrate with a material with greatly expanded active sensing surface area to interact with odorant molecules on top of the substrate.
Figure 2B:
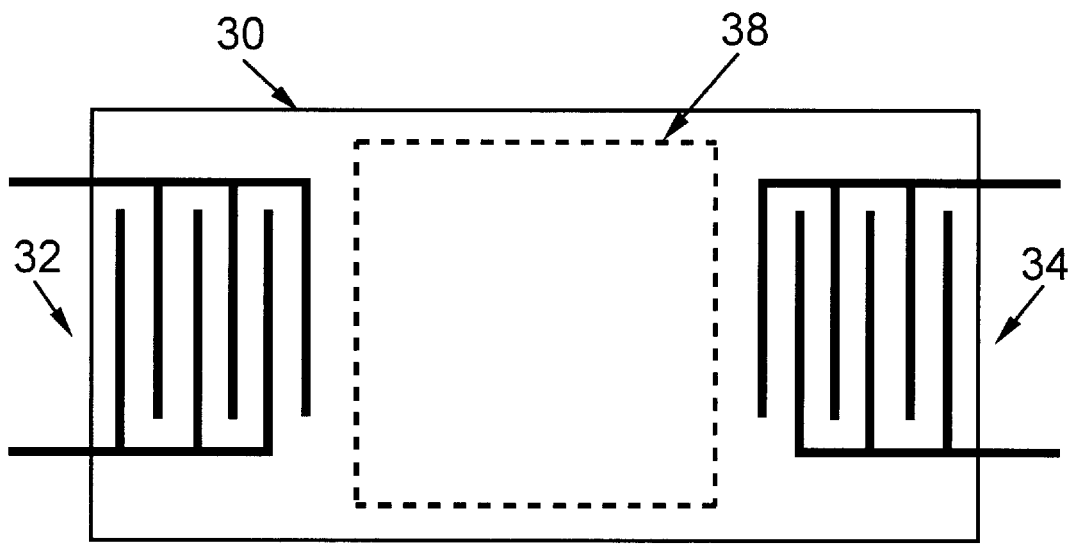
FIG. 2B is a top view of a SAW device with a material with greatly expanded active sensing surface area to interact with odorant molecules on top of the device.

The invention is implemented with a variety of different sensors generally based on a resonator. As shown in FIG. 2A, a sensor element 20 is formed of a substrate 22 to which a pair of electrodes 24, 26 are attached. Substrate 22 is a resonator which oscillates at a nominal resonant frequency. A layer 28 of surface area increasing material is formed on top of resonator 22. Layer 28 also contains an odorant molecule attaching material. When odorant molecules attach to layer 28, the resonant frequency of resonator 22 is changed. In FIG. 2B the sensor substrate is a particular type of resonator, a surface acoustic wave (SAW) device 30. SAW device 30 has a pair of interdigitated electrodes 32, 34. Layer 38 is similar to layer 28 of FIG. 2A.

In a first embodiment of this invention, the sensor consists of a polymercoated aerogel deposited on the surface of a piezoelectric crystal. Like the biological nose, the artificial olfactory system will have many such sensors, each with a different type of polymer or "equivalent material" responding differently to different odorant molecules. The aerogel or any material that can provide very large surface area per unit volume provides the very large surface area for the coating of the polymer, and thus effectively simulates the many same-type olfactory cells and their combined response. The sensor uses differences in the adsorption rates, solubilities of the odor molecules, and degree of swelling to ensure that a variety of different chemicals can be distinguished. A frequency shift detector forms a part of the sensor, and produces a frequency shift output signal.

Figure 3A:
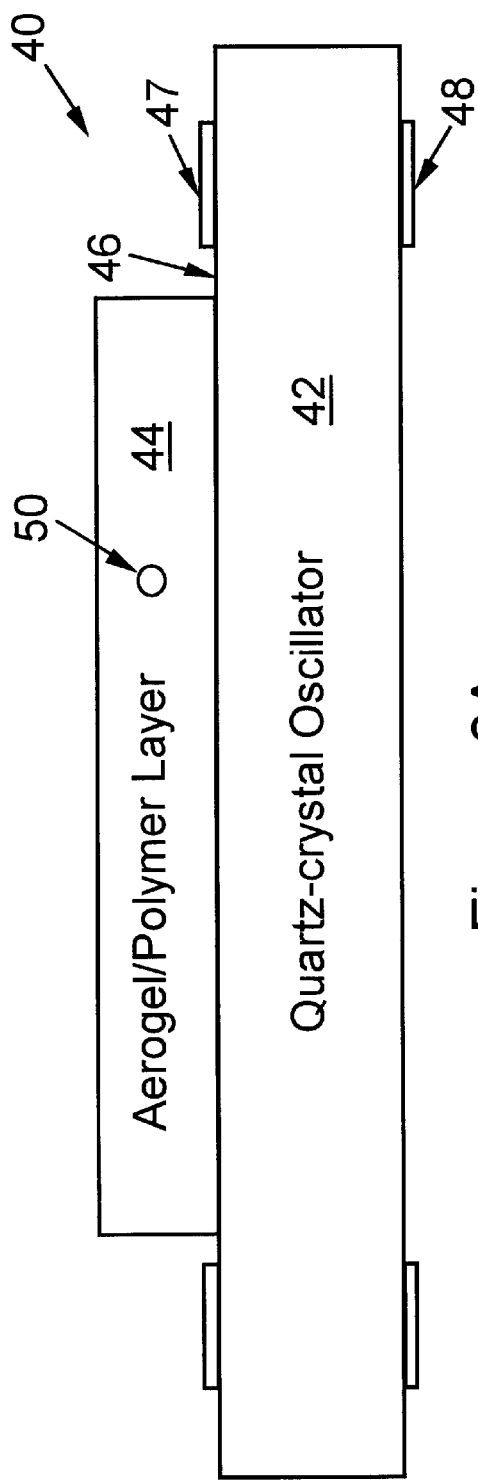
FIG. 3A is a cross sectional view of a sensor having a layer of aerogel, with a polymer coating, on top of a piezoelectric crystal.
Figure 3B:
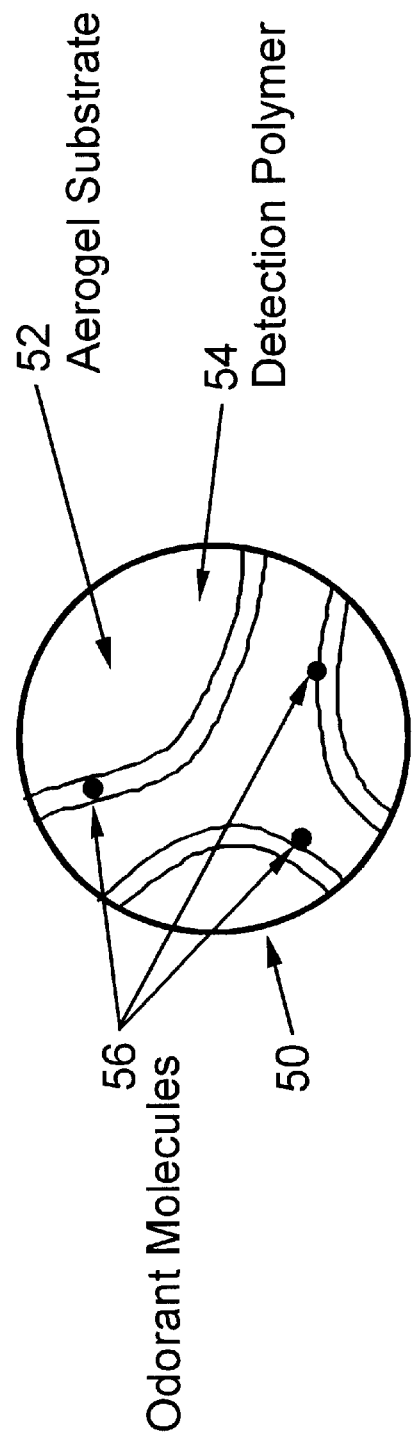
FIG. 3B shows a magnified area of the aerogel/polymer layer of FIG. 3A.

As shown in FIG. 3A, a sensor element 40 is formed from a piezoelectric (PZ) crystal oscillator 42 having an aerogel/polymer layer 44 on a surface 46. A pair of electrodes 47, 48 on opposed surfaces of PZ crystal 42 are used to apply a voltage across the crystal to induce oscillation. Layer 44 provides a high surface area and the ability to capture odorant molecules. A region 50 is shown in greater detail in FIG. 3B. Aerogel substrate 52 has a thin coating of detection polymer 54 thereon. Odorant molecules 56 penetrate void spaces 58 in the aerogel substrate 52. Changes in the resonant frequency of oscillator 42 produced by different odorant molecules are detected. To indirectly detect a substance which does not provide detectable odorant molecules, a reactive material can also be included in the aerogel/polymer layer 44 (or closely nearby) whereby the substance to be detected reacts with the reactive material to produce odorant molecules as a reaction product which can then be detected by the sensor element 40.

Figure 4A:
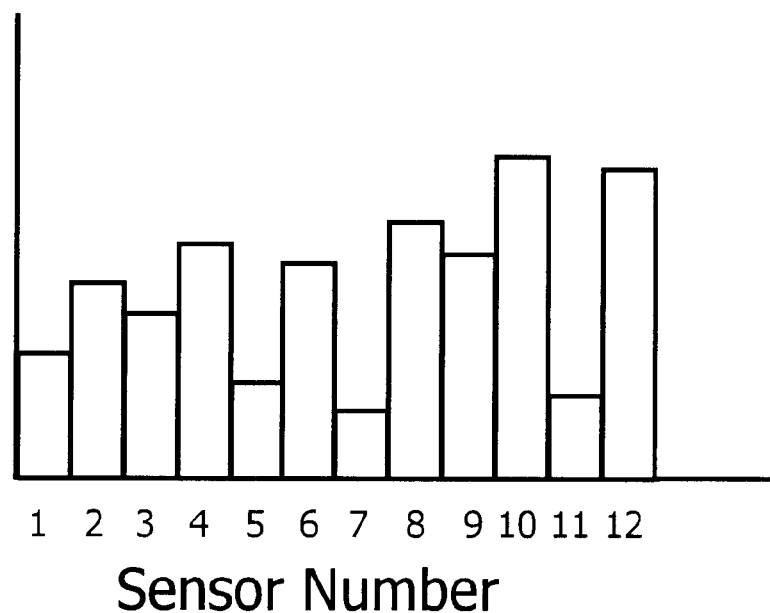
FIG. 4A illustrates the response of twelve different sensors to the same species.
Figure 4B:
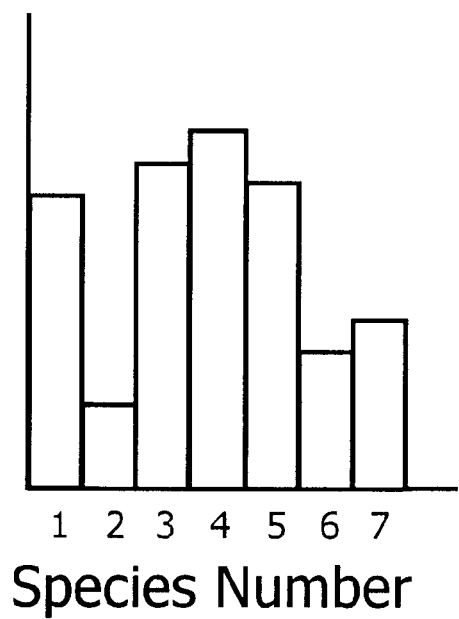
FIG. 4B illustrates the response of one sensor to seven different species.

As shown in FIG. 4A, different sensor elements (e.g., 1–12) respond differently to the same species. As shown in FIG. 4B, each sensor will have a different response to different species (e.g., 1–7). Thus, from the combination of different sensors and responses to different species, an odor signature will be obtained.

The outputs of the frequency shift detectors will be coupled with an artificial neural network for odor discrimination, and possibly for further sensitivity enhancement, as in the case of a biological nose. There are many reasons to employ artificial neural-networks (ANNs) for signal analysis. First, artificial neural networks are inherently very reliable, because like their biological counterparts, information and "knowledge" are distributed and not localized within them. As a result, local damage will not necessarily "kill" the system. Depending on its design, its performance will degrade only slowly until a substantial number of components have failed. Second, ANNs have been demonstrated to be able to extract subtle signals from a noisy environment. Third, neural networks can be used to map out the relationships between different odor signatures and the corresponding compositions as well as the quantities of each of the components in the mixture. Neural networks can go beyond routine pattern recognition. A properly designed ANN has the ability to generalize from the information it "learns" and it thus can respond correctly to unforeseen scenarios. In other words, similar to the canine, the neural network "learns" from the different odor signatures given proper training and then has the potential to generalize beyond that. The ability to generalize is extremely important because of odors from non-targets. For example, one cannot simply teach a neural network or a canine every single non-explosive odor in the world. This is significant because the FAA has repeatedly stressed the importance of minimizing false alarms. If such an alarm occurs in some major airport such as New York City's JFK Airport, it will result in panic and chaos.

From the standpoint of hardware implementation, there is another reason to employ neural-network hardware. Since most sensor outputs are analog in nature, then analog-to-digital converters are needed to interface between the sensors and the CPU if a conventional microprocessor is used. In the future, with addition to the olfactory system of more and more different types of sensors (or equivalently "types of olfactory cells"), hardware complexity, power, as well as cost will substantially increase with the conventional CPU approach. Since low-cost neural-network hardware is an inherently parallel system capable of simultaneously taking in analog signals from many sensors, e.g., 64 and these chips can be cascaded to build systems with even more inputs and outputs, it is ideally suitable for data fusion, as is required for this particular problem, and it will do so without the needs of extra hardware such as A–D converters and multiplexers, thus resulting in greater simplicity and lower cost.

Figure 5:
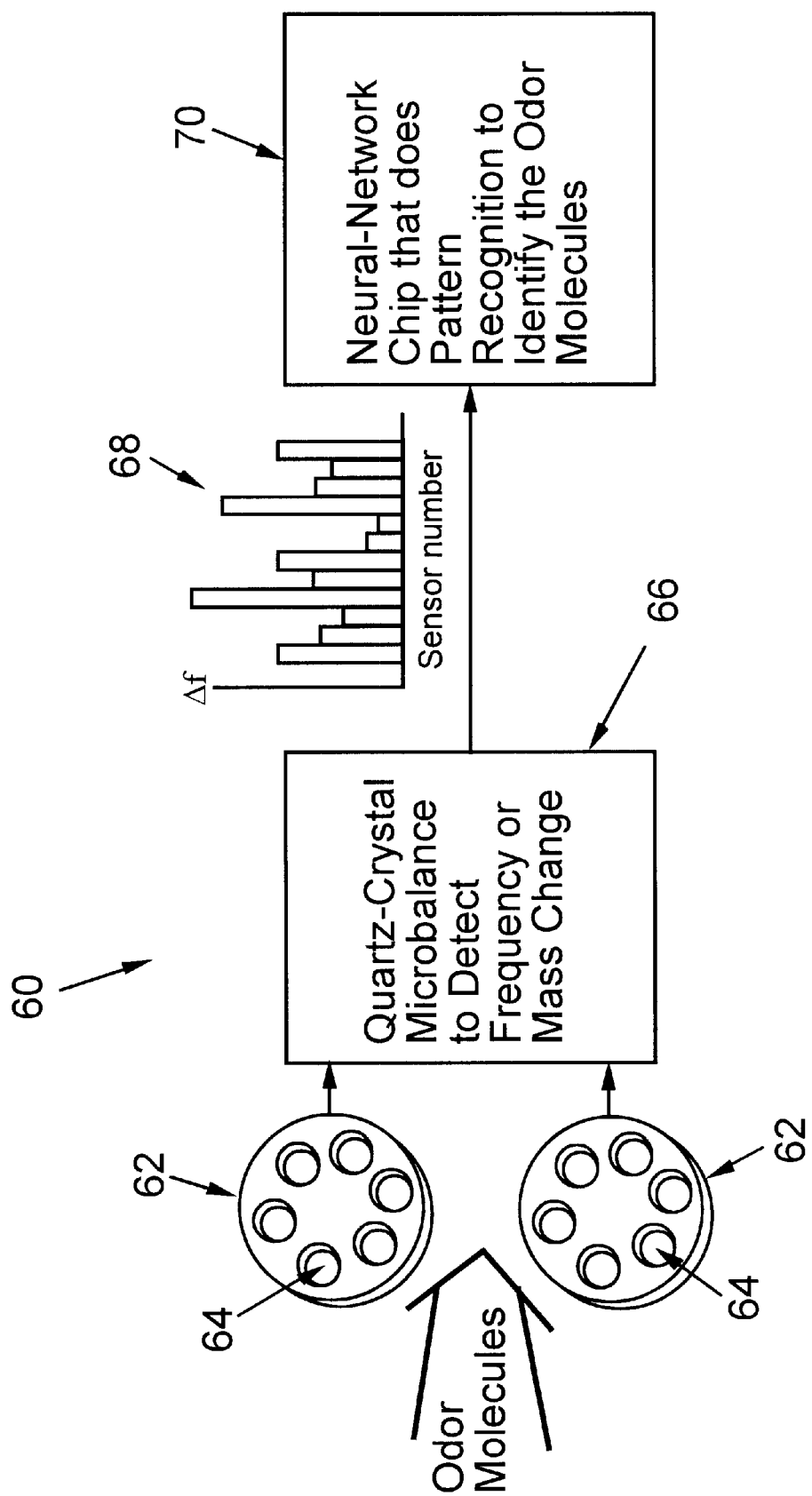
FIG. 5 shows a complete artificial olfactory system with two sensing units, a measurement unit, and a neural network or intelligent processing system.

As shown in FIG. 5, artificial olfactory system 60 has a pair of sensor units 62, each of which contain a plurality (e.g., 6) of sensor elements 64. The outputs of the sensor elements 64 are measured by measurement device 66. Device 66 is a frequency measurement unit, e.g., a quartz crystal microbalance, to detect frequency or mass change. Measurement device 66 produces a signature 68 which is input into an intelligent signal processor 70, e.g., a neural network that performs pattern recognition to detect, recognize and identify the odor molecules.

The most important advantages of this invention of an artificial olfactory system are its potential to achieve very high levels of sensitivity and selectivity, low cost, and small size.

A first embodiment of the electronic nose will be relatively simple, and yet reasonably compact. Off-the-shelf quartz crystals are used as the substrates for the sensors. Using one of the many proven aerogel thin-film deposition methods, a uniform and relatively thick planar xerogel film is formed on the crystal. Deposition of films with thicknesses ranging from one to greater than 200 micrometers is possible. Very uniform deposition is possible, given the relatively small area of the crystal (1.4 cm in diameter), which allows tight control. Some of the aerogels such as the xerogels have open structures while retaining relatively high porosity; this results in a relatively large specific surface area. The resulting large spacings guarantee a good coating of polymer, with sufficient leftover open structure after polymer deposition for good gas-molecule permeability.

A film with a thickness of 50 microns made from xerogel with a specific surface area of 50 sq. meter/gm and a density of 0.7 gm/cc would produce a 1750-fold increase in surface area over an uncoated surface. Since certain aerogel has been demonstrated to have a specific surface area as high as 1160 sq. meter/gm, which is a factor of 23 higher and a porosity of 98%, these parameters can easily be achieved. However, this is clearly just a starting point; through control of sol-gel polymerization, catalysts, and drying procedures, even greater amplification factors can be attained, since the manufacture of aerogels can be controlled to tailor both structure and properties. Also other materials than aerogels can be used to increase the internal surface area. For example, nanotube structures, porous carbons, or zeolites may be used.

The chemical diversity in the types of polymers can readily be obtained through the use of simply-prepared, conventional, polymers such as polydimethylsiloxane, poly(cyanopropyl)methylsiloxane, polyphenylmethylsiloxane, poly(isopropylcarboxylic acid)methylsiloxane, poly(aminopropyl) methylsiloxane, poly(vinyl acetate), poly(vinyl butyral), poly(styrene), poly(sulfone), poly(methyl methacrylate), poly(4-vinylphenol), poly(styrene-co-allyl alcohol), poly(ether urethane), poly(ethylene oxide), poly(caprolactone), poly(N-vinylpyrrolidone), poly(carbonate bisphenol A), and many others. Even more specific types of polymers can be tailored to either a wide variety or a narrow range of odors, such as those from ammunition, explosives, illegal drugs, fuel or exhaust leaks. The preparation and deposition of these polymers is relatively easy. The monomer solution can be diffused into the xerogel, where it will polymerize on the xerogel surfaces. This polymerization will be relatively easy for the coating of the xerogel's surfaces and can be controlled through dilution, catalysts, and other parameters. More sophisticated deposition methods can be used for a tighter degree of control.

Instead of polymers, any other suitable material which attaches the species to be detected can be used. For example, to detect a biological agent such as a virus, a virus attachment material such as an antibody, a protein, or a cell membrane could be used. Also polymers or other suitable materials can be modified by radiation treatments such as ultraviolet or ionic bombardment to enhance their adsorption or absorption characteristics.

For detection and measurement, each of these specially-prepared crystals is connected to equipment that monitors the oscillation of the crystal. To get very accurate measurements, equipment that continually tests and analyzes the phase-frequency relationship of the monitor crystal is used. This system generates a precise frequency and applies it to the crystal. At resonance, the angular phase difference between the applied voltage and the crystal-generated current is zero. Measuring the phase difference determines how much the frequency of the applied voltage should change; the process is repeated thousands of times a second in order to home in on the resonant frequency. The outputs of the detecting equipment will be processed by appropriate neural network algorithms running on a personal computer for odor identification and quantification. With semi-custom integrated circuit design, the bulky frequency measurement equipment (QCM) can be reduced to a single integrated-circuit chip (about 1 cm$^2$). The personal computer running the neural network algorithms will be replaced by appropriate neural-network integrated circuit chip(s) which occupy a small area, e.g., 0.62 cm$^2$, and thus the entire olfactory system will be extremely compact, less than a few cubic inches.

A 50-micron-thick xerogel film should not reduce the fundamental oscillation frequency too much for proper functioning of the QCM. This will depend on the density on the xerogel. A highly-condensed one with a density of 0.7 gm/cm$^3$ will only reduce the system's fundamental frequency from 6 MHz to about 5.5 MHz, with the result that there should be no such problems coming from using such a film or even much thicker films. With even less dense aerogel films for even greater surface area the loading effect on the crystal will diminish.

Using the QCM technique, very thin films can be detected. The minimum thickness is dependent on several factors—the crystal operational frequency, the density, integration time and other factors. In the absence of the aerogel and with an integration time of 1 second assuming an extremely conservative 1-Hz detection resolution, a 6-MHz crystal can detect a thickness of 2 Å of a film with a density of 1 gm/cm$^3$; the sensitivity improves in direct proportion to the integration time. The presence of the aerogel itself possibly makes relatively little change in the sensitivity, because of its relatively light weight, but it introduces the additional factor of a greatly expanded internal area. A xerogel with a density of 0.7 gm/cm$^3$, an internal area of 50 m$^2$/gm, and a thickness of 50 microns will have an internal area of 1750 cm$^2$/cm$^2$, a pure number, called the area multiplier. If the aerogel's internal surface was evenly coated with some adsorbed film, then the effective thickness would be the area multiplier (1750) times the true thickness, meaning that the detectable true thickness would be reduced by a factor of the area multiplier, that is, down to ~0.001 Å.

However, it is necessary to translate this thickness detection limit into concentration. At a thickness of 0.001 Å, the adsorbed molecules are very thinly spread, and are far from achieving a maximum of coverage of the surface. This is because molecules can depart as well as arrive, and if there are insufficient arrivals, molecules depart until the departures become rare enough to be replenished by the arrivals. The state of 100% coverage of all possible adsorption sites is, of course, an asymptotic one, but the state of 50% coverage forms a convenient dividing line between the cases of poor coverage and of saturated coverage. Below that point, the amount of coverage is approximately proportional to the gas-phase concentration, while above it, the coverage goes to one. A calculation of that dividing point is obtained from water adsorbed on silica gel. The dividing point was an abundance of 2% by number of molecules at a temperature of 25° C. So if there is more than 2% of water in air, the silica gel will saturate, while if there is less than that, the amount of coverage of the silica gel will be the ratio of the abundance to 2%. At this point, the coverage fraction implied by an effective thickness of 0.001 Å must be considered. A calculation is obtained from nitrogen, a molecule of which likes to occupy an area of about 15.8 square angstroms on a surface, thus giving an equivalent thickness of about 3 Å for a material with a density of 1 gm/cm$^3$. If a water molecule likes to occupy a similar area, then the equivalent thickness of saturated water is 2 Å instead. This means that one can detect water if its surface coverage is only $\frac{1}{2000}$ of its saturation value, and if the surface has the adsorbing properties of silica gel, then one can detect 10 ppm of water vapor. For the case of detecting nitrogen dioxide, then to first order of calculation the detection limit will be about 4 ppm, because NO$_2$ molecules are about 2.6 times more massive than those of water. Similar calculations result in detection limits of 6 ppm for NO and ~4 ppm for CO$_2$. Furthermore, with an ultra-sensitive QCM, such as an available one with a 0.005 Hz resolution instead of 1 Hz resolution, and with a factor of two as a safety margin, then the corresponding detection limit will be 40–60 ppb for these compounds.

Besides these estimates, a more accurate projection of the performance of the artificial olfactory system can be made using data from W. Gopel and his group in the area of using the QCM approach for the detection of numerous organic solvent vapors as well as carbon dioxide. The present invention is a significant improvement in terms of sensitivity and selectivity, because of the use of aerogels and neural-network or intelligent system technologies. Gopel's work, however, provides substantial and useful information, such as in the area of polymers. Based on his reported experimental results, a sensitivity of ~16 ppb for chemicals such as CO$_2$ is calculated using the present approach. This number agrees with the 40–60 ppb number derived earlier. An additional factor of 100–10,000 gain in performance can be produced by optimizing the many factors that control the overall sensor's sensitivity. For that reason, it is possible to reach a sensitivity of as low as 10 part per trillion without using preconcentration. For example, with an artificial neural network designed to operate at the level of claimed biological capability stated earlier, the sensitivity can be enhanced by three orders of magnitude. As a result, a single parameter improvement alone may give a factor 1000 improvement in sensitivity. Furthermore, the polymer used by Gopel turns out to be extremely sensitive to NO$_2$; in fact its sensitivity is a factor of 50 times more than that of CO$_2$. In addition, it is possible to have further enhancement of sensitivity through pre-concentration by as much as a factor of 600, as is done to increase sensitivity of various detection systems. Thus, less than one part per trillion sensitivity should be feasible. In addition, the invention can use a new approach for pre-concentration, using aerogel, which may be much simpler than that of cryogenic pre-concentration.

The issues of humidity and temperature effects can be compensated or corrected by including humidity and temperature sensors and through the use of the neural network to learn the odor patterns under various combinations of temperature and humidity conditions. These learned patterns can then be used to correct for the impact of humidity and temperature.

The invention utilizes two areas of technology to achieve the high sensitivity and selectivity, aerogel technology and neural network technology.

Aerogels, both inorganic and organic, are solid foams that can be so low in density that they are mostly empty space—no more substantial than frozen smoke. They are open-cell structures like a sponge. A xerogel is a higher density and lower porosity form of aerogel. The first aerogels—silica aerogels, highly porous forms of silica or silicon dioxide (SiO$_2$)—were made in the 1930's, but it was not until the 1970's that they were put to practical uses. Organic (carbon-based) aerogels have a lower average atomic number than silica aerogels, and have potential advantages in certain applications. Carbon organic aerogels are the stiffest of all types.

Aerogel synthesis is basically a process of polymerization, beginning with simple molecules and bonding them together to make a giant crosslinked molecule. The production of aerogel proceeds through stages. It begins as a colloidal solution made up of a liquid within which ultrafine particles are uniformly dispersed. Its next stage is a gel, a colloidal system of liquid and solid phases that is very nearly a solid. The final phase is a low-density, highly porous solid; it is achieved by carefully drying the gel without collapsing the fragile polymer network of the solid.

In a typical solution-gel or "sol-gel" polymerization, a multifunctional monomer is polymerized in solution and proceeds through three stages:
1) The starting monomer (<1 nm in diameter) undergoes hydrolysis or addition reactions at some of its available reaction sites.
2) The substituted molecules then condense into small clusters (1–20 nm in diameter). The clusters will be polymer-like or colloid-like in structure, depending on the degree of crosslinking and the growth processes by which they were formed. They contain surface functional groups (e.g., Si—OH, and —CH$_2$OH) that can link clusters together with covalent bonds.
3) Finally, through widespread crosslinking among clusters, a transparent gel is formed. The gel is composed of two phases—an interconnected solid and a liquid that fills the pores.

Supercritical drying of the wet gel produces the aerogel. This can be done by raising the temperature and pressure of the solvent above its critical point; in its supercritical state, the solvent becomes a gas-like fluid and can escape from the crosslinked gel network without damaging it.

The structure and properties of the final, dried aerogel are dictated by the conditions during polymerization. Factors such as the temperature, the pH of the solution (the level of acidification), the type of catalyst, and the ratio of reactant to solvent influence the crosslinking chemistry and growth processes that take place before gelation. The microstructure of the aerogel is derived from the structure of the wet gel after supercritical extraction of the solvent. Thus, by controlling the reaction conditions during polymerization, crosslinking, and supercritical solvent extraction, the structure and properties of aerogels can be extensively tailored.

To synthesize a silica aerogel, begin with a metal alkoxide (a compound formed by the reaction of a metal chloride with alcohol), which is submitted to alteration or decomposition by water (hydrolysis) and transformed from the monomer to a crosslinked gel network (condensation). Inorganic aerogels have been prepared from monomers such as tetraisopropoxytitanate, aluminum secbutylate, and zirconium isopropoxide, but mostly from the sol-gel polymerization of tetranethoxysilane (TMOS) or the less toxic tetraethoxysilane (TEOS).

Organic aerogels contain mainly carbon and hydrogen atoms and thus have a lower average atomic number (Z). In most other respects (e.g., reaction pathways, microstructure, and other properties), they are very similar to the silica aerogels. Example of organic aerogels are resorcinol-formaldehyde, melamine-formaldehyde, and carbon (obtained by pyrolyzing resorcinol-formaldehyde at 1100° C.). Resorcinol-formaldehyde aerogels can be pyrolyzed in an inert atmosphere to form pure carbon aerogels, which have improved mechanical properties and thermal expansion coefficients. During the pyrolysis cycle, the aerogels undergo substantial shrinkage as gaseous byproducts are evolved and the vitreous carbon matrix is formed. The carbon aerogels are black and opaque and are about 10 times stiffer than the uncarbonized material at an equivalent density. Increased stiffness yields improved machinability; carbonized aerogels have been machined into intricate shapes.

In most low-density materials derived from phase-separation or replication processes, structure and properties are controlled at the 1- to 100-micron scale. However, the solution chemistry of aerogels can be controlled to tailor structure and properties. Parameters such as density, surface area, cell/pore size, mechanical properties, optical transmission, refractive index, and chemical composition must be controlled in both inorganic and organic aerogels. The chief process variables that affect the structure and properties of aerogels are the type and concentration of the catalyst, the ratio of solvent to reactant, and the drying procedure.

An ultra low-density silica aerogel, an inorganic polymer foam that is nearly transparent and ghostlike in appearance, has been developed with a density of 0.003 g/cm$^3$ (only three times the density of air) and yet it is so strong that it can support 1600 times its weight!

The structure and properties of the finished materials can be tailored by controlling the conditions during polymerization, to make strong, high-density aerogels as well as extremely transparent, ultralow-density aerogels. These materials enable the formation of sensor elements for the artificial olfactory system of the invention.

In nature, part of the functions of the olfactory bulb and the brain is to extract information from noisy signals. If the detected concentration is extremely low, then the corresponding signal-to-noise ratio coming out from the receptor cells will be poor. As a result, it will be desirable to have some signal-processing technique that can extract signals from a noisy environment. Artificial neural networks can be used to clean up noisy signals. Thus, for very low signal levels with serious interference as may be the case for very low level odor detection, which has very low signal-to-noise ratios, neural networks are well suited for signal extraction.

Once the detected signals from the sensors reach a steady stage, every sensor should theoretically give the same level of signal as a function of time. As a result, every scan on all the sensors (a snapshot in the time domain) should give the same pattern or signature except for noise. This perturbation of the signature by noise can be cleaned up first by transforming the signal into the frequency domain through Fast Fourier Transform for signal filtration, then followed by a reverse transform back into the time domain with further filtering through an auto-associative neural network. A low-pass filter gives a small improvement, but a neural-network filter achieves a much greater improvement.

In addition to signal extraction, pattern recognition and generalization from learned patterns to handle unforeseen scenarios are two other valuable aspects of neural networks. Complicated pattern-recognition tasks and the learning of input-output correlations by using neural networks to recognize different odor signatures and correlating that signature with the corresponding compound can be performed.

Very similar signatures can still be effectively identified using neural networks and other intelligent systems. A standard backpropagation neural network can be used to identify extremely similar signatures or signal patterns. A neural network can be trained to recognize signal patterns or signatures and to correlate each signature back to its corresponding causing condition. Furthermore, after training, the neural network can predict correctly from "unseen" signals.

This "self-learning" capability represents a fundamental difference between neural networks and other "intelligent" systems such as an expert system. This capability is significant, because one may actually learn from the network and gain a better understanding of the system. As more data are available, such a system may behave more and more intelligently. In addition, out of all the channels, the network can select automatically the channels in groups, possibly because it is attempting to take into account the drifts of the channels and thus when it looks for a specific signal peak, it will look not only at that particular channel but also the adjacent channels to account for drift.

With a set of training data, an intelligent system that outperforms standard neural networks can be produced. In the neural-network approach, for example, a large number of synaptic weights might be used to describe the different odor signatures. An intelligent system may use a much smaller number of parameters to achieve the same goal. Like the basic neural-network approach, these parameters are automatically generated through a learning process. Unlike traditional neural networks which learn the input-output relationship almost by "brute force", the intelligent system uses human knowledge or higher-level descriptions to enforce additional constraints, thus a more compact description. The large number of synaptic weights used by a standard back-propagation network represent a "brute force" approach with enough fitting parameters to guarantee a good "fit"; whereas the intelligent system with a much smaller number of parameters to achieve the same result should be able to generalize far better and thus learn more effectively because there is fewer degrees of freedom.

The ability to perform data fusion from many channels, to take into account the drifts of the signals, to extract signals from noisy environment, to recognize patterns or signatures and finally to generalize to unforeseen scenarios are exactly the essential attributes that one speculates that the brain and the natural olfactory system exercise during the course of processing odor recognition, and thus is an important component of the artificial neural network for the artificial olfactory system.

For signal-processing applications where real-time response and cost-to-performance and weight-to-performance ratios are important, artificial-neural-networks chips, being massively parallel and robust, are preferred. An artificial neural network chip has been developed, using thin-film resistors as artificial synapses and operational amplifiers as artificial neurons to produce customizable, very-large-scale artificial neural network chips and/or systems. A neural-network chip consists of three major components—a synaptic array, input-buffer amplifiers, and output neurons. An example is a fully-integrated, cascadable, programmable neural-network chip (0.84 by 0.74 cm$^2$) designed to be capable of a performance of 200 million interconnects per second, having 64 input-buffer amplifiers for 64 inputs and 32 output neurons with all inputs and outputs fully connected through the synaptic array.

The chip has a number of significant advantages. For example, the inputs are high-impedance, high-current drive-buffer amplifiers to allow the chip to drive other chips, thus making the chip cascadable. This provides the foundation for building system level of performance using the chip as a building block. The synaptic array is programmable, highly uniform, densely packed, fully-connected and can accept both excitatory and inhibitory inputs. The high resistance (2 megaohm) of the synaptic technology keeps the overall power consumption very low, and the small size (10 micron by 10 micron) of the resistors representing the synapses significantly minimizes the very expensive real estate of the integrated chip, thus substantially lowering the cost of the chip, since the cost of an integrated-circuit chip increases rapidly with the size of the chip. Another unique contribution is the use of identical resistors to form synapses of different strengths. Using an 8-bit binary-weighted representation of a synapse, 256 synaptic strengths can be defined with just eight identical resistors. Thus instead of fabricating different synapses, an array of identical resistors is fabricated; greatly simplify the process. Unlike laser trimming which needs to be extremely precise to define the strength of a resistor, each synapse is defined by either leaving connected or isolating each of the eight resistors. This greatly simplifies the process of programming synaptic strength. Programming these neural networks can be easily accomplished using precision laser cutting or by more conventional integrated-circuit processing technology that employs only one mask. The laser-programming technology allows fast turnaround for rapid prototyping and insertion, on the order of hours. The conventional type of one-mask programming allows the use of more conventional semiconductor technology to program the entire wafer, laying the foundation for volume production. In addition, because the synapses are built independently of the substrate, the chip can be three-dimensional with the synapses stacked on top of the neurons. Such a 3-D structure could be cost-effective and extremely compact. In addition, the large dynamic range of the linear behavior of the synapses provides a wide margin for the design of the neurons. The 32 output neurons are capable for both excitatory and inhibitory functions, with each of the neurons capable of a programmable gain from one to 1024. This allows the great flexibility of having multiple transfer functions on a single layer, and also allows implementation of multi-layer networks on a single-layer neural network chip. The four-stage driver in each of the neurons allows high capacity to drive other circuitry.

Based on modification of the current chip, a $10 to $25 per chip before packaging with a capability of 5 billion interconnects per second is possible in the future, providing enormous data fusion, extremely fast parallel computation, intelligence, and also inherent reliability similar to biological neural networks. Though this immense amount of processing power may seem like overkill, once it is available, a general purpose olfactory system with a thousand sensors will make full use of such a powerful chip. But at least a lesser design is sufficient to address the needs of a simple artificial olfactory system intended for applications described above.

A basic system, which incorporates the principles and features described herein includes the following major components.

Figure 6A:
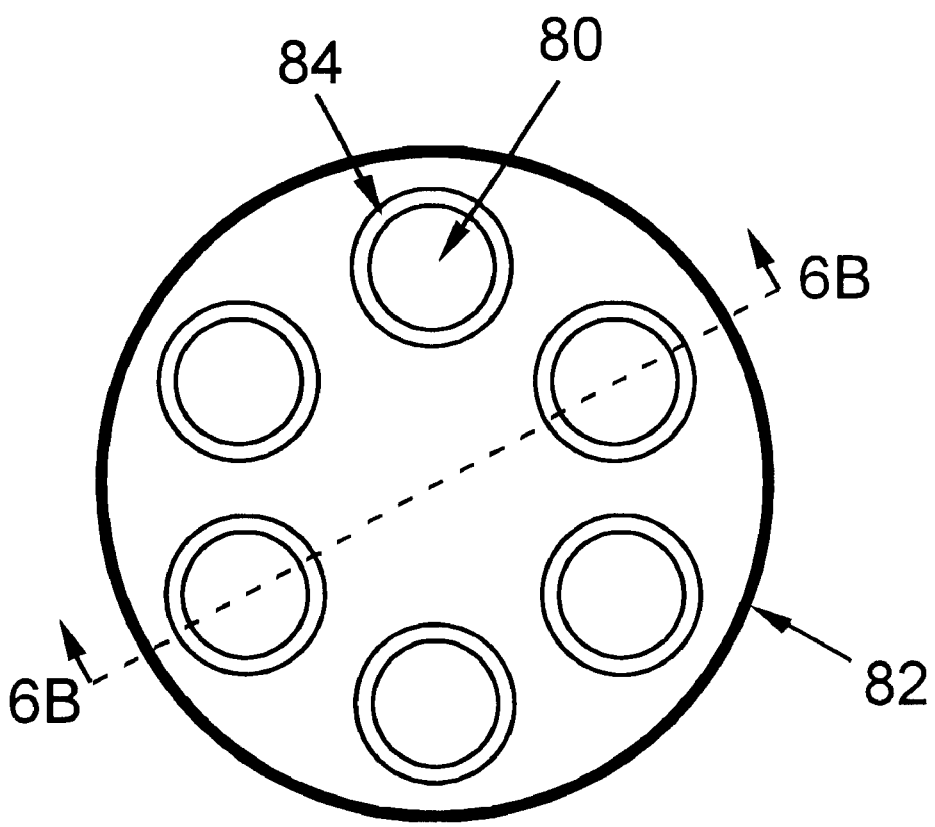
FIGS. 6A, B are top and sectional side views of a sensor unit with six sensor elements.
Figure 6B:
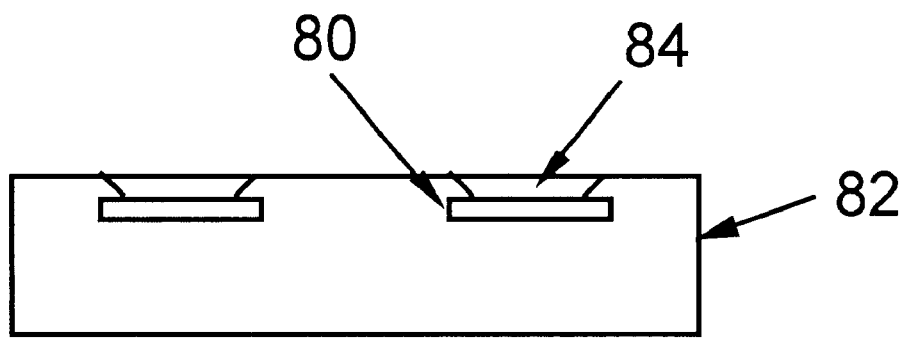

1) Hardware—Two six-sensor units, as shown in FIGS. 6A, B each measuring ~3.5 inches in diameter and 2 inches thick, provide of a total of 12 sensors. Six crystals 80 are contained in a circular housing 82 in openings 84. The sensor units are integrated with the QCM equipment which is interfaced with a personal computer (PC) through appropriate data interface circuit.

2) Software—Neural networks are implemented on the personal computer (PC) for the analysis of both the detection limits and the resolving power of the olfactory system.

The entire olfactory system is a self-contained unit which consists of the two sensor units and two boxes, one for the QCM equipment and the other for the PC, each about 19 in. by 19 in. by 6 in.

From this basic configuration, more advanced configurations can be produced. Miniaturization of the quartz crystals such as using surface acoustic wave (SAW) devices or resonant micro-mechanical structures based on integrated circuit microfabrication will allow more compact and low-power devices. Thousands of types of sensors can be accommodated on a chip and thus will have even wider range of detection capabilities and improve selectivity. This IC chip approach will significantly reduce the cost to the order of $10 per chip. Improvement in detection limits will also greatly enhance sensitivity. This may be feasible as a result of structural design of the sensors, aerogels, polymers, and signal enhancement using neural networks. Examples of these are making the crystal thinner, employing SAW or micro-machined devices which can operate at much higher frequencies than bulk quartz crystals, and using appropriate aerogels which in general have much higher degrees of porosity than xerogels or other "equivalent" substance such as nanotubes, porous carbons or zeolites, thus increasing its surface area per unit volume. Simple improvement such as using much thicker xerogel films and coating both sides of the crystals will improve sensitivity by a factor of eight. Longer integration time will also enhance sensitivity. Further improvement in this sensitivity is possible through various other means such as trading off between selectivity and sensitivity by using lock-and-key systems.

The QCM equipment could be replaced by a custom-designed chip or chip set, thus again further reducing the cost and size of the system. One can implement neural-network algorithms in a digital-signal-processing chip to get the flexibility to alter algorithms as more efficient algorithms become available, or directly on a low-power neural network chip such as ours for possible battery operation.

As a result, a low-cost, ultra-sensitive, highly miniaturized (concealable), battery-powered, electronic chemical-sensing system can be provided that would cost on the order of ten to a few hundred of dollars in a package consisting of a few chips about a few $cm^2$ (excluding the battery) with a detection limit of 100 parts per trillion or less without pre-concentration.

Changes and modifications in the specifically described embodiments can be carried out without departing from the scope of the invention which is intended to be limited only by the scope of the appended claims.

I claim:

1. A sensor element for an artificial olfactory system, comprising: a sensor substrate; a layer of surface area increasing material on a surface of the substrate; a coating of odorant molecule attachment material on the layer of surface area increasing material; wherein the surface area increasing material is an aerogel, a porous carbon, or a nanotube.

2. The sensor element of claim 1 wherein the odorant molecule attachment material is a polymer.

3. The sensor element of claim 1 wherein the odorant molecule attachment material is a radiation treated material.

4. The sensor element of claim 1 wherein the sensor substrate is a resonator.

5. The sensor element of claim 1 wherein the sensor substrate is a piezoelectric crystal, a surface acoustic wave (SAW) device, or a micro-machined resonator.

6. The sensor element of claim 1 wherein the odorant molecule attachment material is a virus attachment material.

7. The sensor element of claim 1 wherein the odorant molecule attachment material is an antibody, a protein, or a cell membrane.

8. The sensor element of claim 1 further comprising a reactive material operatively associated with the sensor substrate for reacting with a substance to be detected to produce detectable odorant molecules.

9. An artificial olfactory system, comprising: a plurality of sensor elements, each comprising a sensor substrate, a layer of surface area increasing material on a surface of the substrate, a coating of odorant molecule attachment material on the layer of surface area increasing material, wherein the surface area increasing material is an aerogel, a porous carbon, or a nanotube; a measurement device connected to the plurality of sensor elements to detect changes produced by the presence of odorant molecules; a signal processor connected to the measurement device.

10. The artificial olfactory system of claim 9 wherein the measurement device is a frequency shift detector which detects changes in the resonant frequency of each sensor element.

11. The artificial olfactory system of claim 9 wherein the signal processor is an artificial neural network.

12. The artificial olfactory system of claim 9 wherein the odorant molecule attachment material is a polymer.

13. The artificial olfactory system of claim 9 wherein the odorant molecule attachment material is a radiation treated material.

14. The artificial olfactory system of claim 9 wherein the odorant molecule attachment material is a virus attachment material.

15. The artificial olfactory system of claim 9 wherein the odorant molecule attachment material is an antibody, a protein, or a cell membrane.

16. The artificial olfactory system of claim 9 further comprising a reactive material operatively associated with the sensor substrate for reacting with a substance to be detected to produce detectable odorant molecules.

* * * * *